United States Patent [19]
Yanai et al.

[11] Patent Number: 6,030,116
[45] Date of Patent: Feb. 29, 2000

[54] HEAT AND MOISTURE TRANSFER CHARACTERISTIC MEASURING EQUIPMENT

[75] Inventors: Yuichi Yanai; Mitsuo Sobajima; Tomiko Shiji, all of Aichi, Japan

[73] Assignee: Nisshinbo Industries, Inc., Tokyo, Japan

[21] Appl. No.: 08/880,882

[22] Filed: Jun. 23, 1997

[30]  Foreign Application Priority Data

Jun. 27, 1996 [JP] Japan ................................. 8-188955

[51] Int. Cl.[7] .......................... G01K 17/00; G01N 25/20; G01N 25/56
[52] U.S. Cl. ................................ 374/142; 374/43; 374/54
[58] Field of Search ................................. 374/142, 54, 43

[56]  References Cited

U.S. PATENT DOCUMENTS 5,634,718  6/1997  Martinis et al. ........................ 374/142

FOREIGN PATENT DOCUMENTS

| 0102148 | 8/1979 | Japan | 374/142 |
| 0157677 | 12/1979 | Japan | 374/142 |
| 0015146 | 1/1983 | Japan | 374/142 |
| 0116506 | 7/1984 | Japan | 374/142 |
| 0173742 | 10/1984 | Japan | 374/142 |
| 0213761 | 9/1986 | Japan | 374/142 |

*Primary Examiner*—Christopher W. Fulton
*Assistant Examiner*—Quyen Doan
*Attorney, Agent, or Firm*—Kubovcik & Kubovcik

[57]  ABSTRACT

A system capable of measuring the heat and moisture transfer characteristics of thin materials such as clothing materials and the like simultaneously and accurately so as to obtain data for evaluating the suitableness of such material, for clothing. The sample 50 is set to partition the spaces 56 and 57, then the first and second types of air 1 and 2 which have been adjusted to the desired temperature and humidity flow into the temperature and humidity variation measurement section 53 in the desired amounts, respectively. The airs 1 and 2 are brought into contact with the temperature sensor 58 and the humidity sensor 59 at the inlet and outlet port of the section 53. An exchange of heat and moisture takes place between the air 1 and the air 2 through the sample 50. By measuring the temperature and humidity of the airs 1 and 2 at the inlet and outlet ports of the section 53, it is possible to understand the heat and moisture transfer characteristics of the sample 50. By varying the airs 1 and 2 to correspond to various temperature and humidity conditions at the outside and inside of a wearer's clothing, it is possible to measure the variations of the temperature and humidity of the air taking place through the sample 50 simultaneously and in a time-based manner.

7 Claims, 7 Drawing Sheets

HEAT AND MOISTURE TRANSFER CHARACTERISTIC MEASURING EQUIPMENT

TECHNICAL FIELD OF THE INVENTION

The present invention relates to a system for measuring the heat and moisture transfer characteristics of thin materials such as cloth and the like so as to contribute to the evaluation of the materials.

PRIOR ART AND PROBLEMS TO BE SOLVED BY THE INVENTION

Conventionally, the idea of designing and manufacturing daily necessities on the basis of scientific data has been considered important in the industry concerned and the Human Sensory Measurement Application Technology Development Project which is now being executed under the guidance of the Ministry of International Trade and Industry in Japan is one of the activities based on such an idea.

As one of the items which can be a target object to be taken up in the above-mentioned project, there is considered clothing, and as regards clothing, it is desired to precisely measure the heat and moisture transfer characteristics, which are particularly important in the various functions of clothing, especially with respect to the relationship between the two. As methods for measuring the characteristics of clothing, i.e., the cloth, with respect to the transfer of heat and moisture through it, there are prescribed in the Japanese Industrial Standards methods for measuring the drying property (JIS L 1096), warmth retaining property ( JIS L 1096) and water vapor permeability (JIS L 1099) and all of these methods are performed in such a way that a target cloth is placed under a certain condition for a predetermined period of time and when the cloth is held in a steady state, the characteristics of the cloth with respect to moisture and heat are measured separately.

However, when one actually puts on clothing, since the clothing is always subjected to rapid and sharp fluctuations due to body respiration, perspiration, body motion and the external air currents, it is almost impossible to consider that the external environment and the minute space between clothing and the body of the wearer are brought under a steady state. Accordingly, in order to manufacture and supply comfortable clothing from the point of view of the human sensory measurement application technology, it is necessary to measure the characteristics of a cloth as a basic material of the clothing in a state in which the heat and moisture of the cloth are transitional.

As is well known, heat and moisture are not independent of each other in the same environment but act on each other, so that it is not possible to analyze the evaluation of the system of the environment-clothing-human body in which the actions of both heat and moisture coexist, from only individual measurements. Therefore, it is desired to provide a system which is capable of measuring both the heat and the moisture included in the clothing simultaneously and in an unsteady state thereby contributing to the evaluation of the above-mentioned system of the environment clothing-human body.

Figure 1:
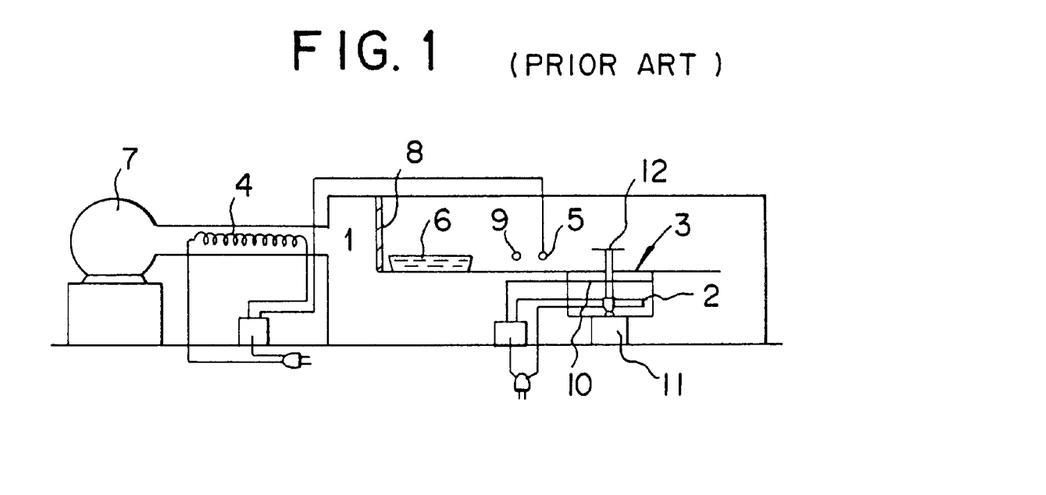
FIG. 1 is a conceptual view of a conventional heat and moisture transfer characteristic measurement system.

Several proposals have already been made with respect to a system for measuring the heat and moisture transfer characteristics of a clothing material. For example, a system disclosed by TOYOBO Co., Ltd. in 1983 (refer to Japanese Patent Publication No. Heisei 1(1989)-19540) can measure the moisture and heat transfer characteristics of the space within an item of clothing by controlling the conditions of the environment and a simulated skin plate. This system is shown in FIG. 1 wherein reference numeral 1 designates a wind duct, reference numeral 2 designates a reproduced human body condition section, reference numeral 3 designates a climate section within the clothing material, reference numeral 4 designates a heater, reference numeral 5 designates a thermostat, reference numeral 6 designates humidity control water, reference numeral 7 designates a blower, reference numeral 8 designates a rectifier, reference numeral 9 designates an anemometer, reference numeral 10 designates a simulated skin plate forming itself into a simulated skin surface, reference numeral 11 designates a magnetic stirrer and reference numeral 12 designates a piston.

In the case of this system or method, temperature and humidity measurement sensors are provided within a space defined by the simulated skin plate and the surface of the sample to thereby obtain data. However, the system or method has the problem that due to the smallness of the simulated skin surface and the minuteness of the space between the simulated skin surface and the sample surface, when the measurement sensors are mounted in the space, the original state of the minute space is disturbed and, as a result, there arises a great possibility that the resultant measured values differ from the temperature and humidity data sought to be evaluated.

Figure 2:
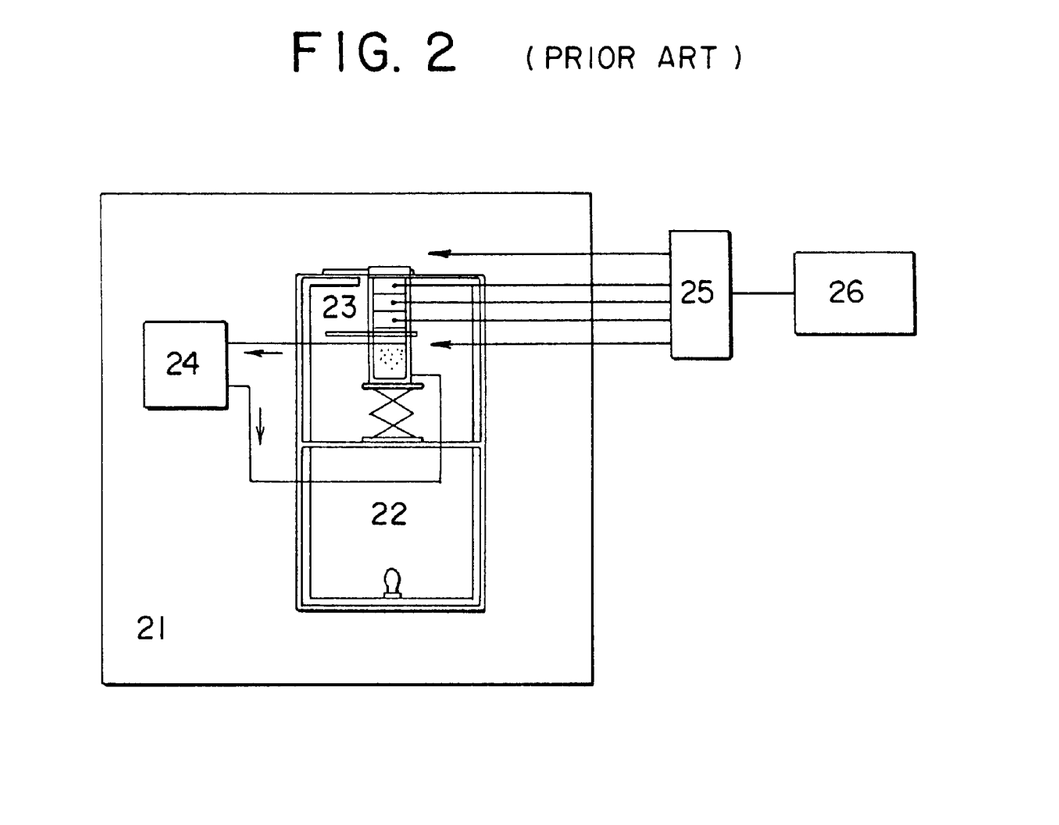
FIG. 2 is a conceptual view of another conventional heat and moisture transfer characteristic measurement system.

Further, the system and method disclosed after 1991 by Professor Yasuda et al of Mukogawa Women's University (Textile Res. J. Vol. 61, Jan. 1991, Vol. 62, April, 1992 and Vol. 64, August, 1994) employs a structure similar to that which is used in an experiment of the gas permeability of a molecular membrane in such that temperature and humidity sensors are respectively set within three small spaces partitioned by items of a clothing material and the external environment so as to observe in sequence how the external environment, having predetermined temperature and humidity values, effects the three spaces. This system or method is shown in FIG. 2 wherein reference numeral 21 designates an environment control chamber, reference numeral 22 designates a thermostat temperature adjustment chamber, reference numeral 23 designates a diffusion column, reference numeral 24 designates a constant temperature tank, reference numeral 25 designates a data collector and reference numeral 26 designates a computer.

However, the above-mentioned system or method has the problem that since the quantity of air is small, a disturbance of the target object to be measured by the temperature and humidity sensors may take place and the conditions of the target object at the time when the environmental temperature and humidity changes rapidly cannot be observed.

Figure 3:
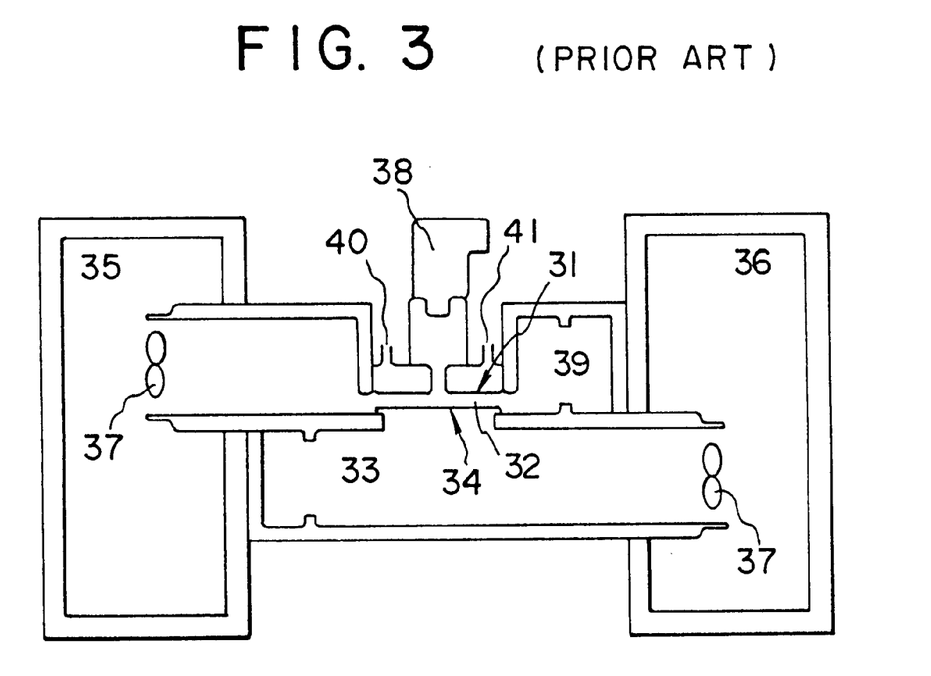
FIG. 3 is a conceptual view of a further conventional heat and moisture transfer characteristic measurement system.

Further, the system and method disclosed by KAO Corporation in 1991 (Fiber Society Journal, Vol. 47, June, 1991) observe the temperature varying condition of a clothing material in such a manner that two types of air having a precisely controlled different temperature and humidity value flow on both sides of the clothing material and the temperature and the humidity of one of the air types is varied. This system is shown in FIG. 3 wherein reference numeral 31 designates a human body section, reference numeral 32 designates an internal environment section, reference numeral 33 designates an external environment section, reference numeral 34 designates a sample cloth, reference numerals 35 and 36 respectively designate a constant temperature device and a constant humidity device, reference numeral 37 designates a fan, reference numeral 38 designates a radiation thermometer, reference numeral 39 designates a temperature and humidity sensor, reference numeral 40 designates an injection port of a constant temperature water and reference numeral 41 designates an exhaust port for the constant temperature water.

The above-mentioned KAO system and method have the problems that although the variation of the temperature of the clothing material itself due to the absorption and discharge of moisture by the material can be observed, since the quantity of air with respect to the material is too large, the quantity of moisture passing through the material is hardly measured and the variations of the temperature and humidity of the material cannot be observed in a short time when counted by seconds due to the capacity of the temperature and humidity control device.

The present invention has been made in view of the above-described problems and an object of the invention is to provide a system which is capable of measuring the heat and moisture transfer characteristics of thin materials such as a clothing material and the like simultaneously and accurately, making clear how a sample material can meet rapid changes in the temperature and humidity of a space outside or inside the material and obtaining basic data for manufacturing comfortable clothing which, of our daily necessities, is the closest to our life.

MEANS TO SOLVE THE PROBLEMS

A first embodiment of the present invention provides a heat and moisture transfer characteristic measurement system comprising means for forming a pair of laminar spaces on both sides of a target sample material to be measured, respectively, a pair of means for allowing two types of air each adjusted to have predetermined temperature and humidity values to pass through the pair of laminar spaces, respectively, and means for detecting temperature and humidity changes in each of the spaces.

In a second embodiment of the invention one of the pair of air supply means is provided with two conditioned air supply units and a changeover device capable of switching between the air supply units so as to instantaneously supply air types having different temperature and humidity values.

In a third embodiment of the invention the heat and moisture transfer characteristic measurement system includes at least means for varying condition of the space forming means with respect to its setting surface.

In a fourth embodiment of the invention the above-mentioned space forming means is provided with means for dripping water-drops onto the target sample to be measured.

In a fifth embodiment of the invention a plurality of temperature and humidity detection means of the heat and moisture transfer characteristic measurement system are provided at an inlet and an outlet sides of each of the spaces whereby the variations of the temperature and humidity of the air types generated as a result of the transfer of heat and moisture between the air types passing through the spaces and the target sample to be measured can be detected.

In a sixth embodiment of the invention the pair of air supply means can be attached to the space forming means from the side of either one of the pair of laminar spaces.

In a seventh embodiment of the invention each of the pair of spaces has a thickness of less than 15 mm.

In a eighth embodiment of the invention a sample holder is removably provided between the pair of laminar spaces, and the jig has an opening capable of causing the target sample mounted on the jig to be exposed to any of the laminar spaces.

In a ninth embodiment of the invention an area of the opening of the sample mounting jig is 10 cm$^2$ or more.

In a tenth embodiment of the invention the number of pairs of the laminar spaces is two or more.

BRIEF DESCRIPTION OF THE SYMBOLS

| | |
|---|---|
| 50 | a sample |
| 51, 52A, 52B | a conditioned air supply devices |
| 53 | a temperature and humidity measurement section |
| 54 | a switching deviee |
| 55 | a flow rate adjuster |
| 56, 57 | a laminar space |
| 58 | a temperature sensor |
| 59 | a humidity sensor |
| 60 | a heat insulating member |
| 61 | a space angle adjustment handle |
| 62 | a sample holder |
| 63 | a holder body |
| 64 | a sample stop frame |
| 65 | an opening |
| 66 | a concave portion |
| 67 | an opening |
| 68 | a handle |
| 69 | a projection |
| 70 | a set screw |
| 71 | a lower side portion |
| 72 | a laminar space thickness adjustment plate |

PREFERRED EMBODIMENTS OF THE INVENTION AND EXPERIMENTAL EXAMPLE

The preferred embodiments of the present invention will now be described with reference to the accompanying drawings.

Figure 4:
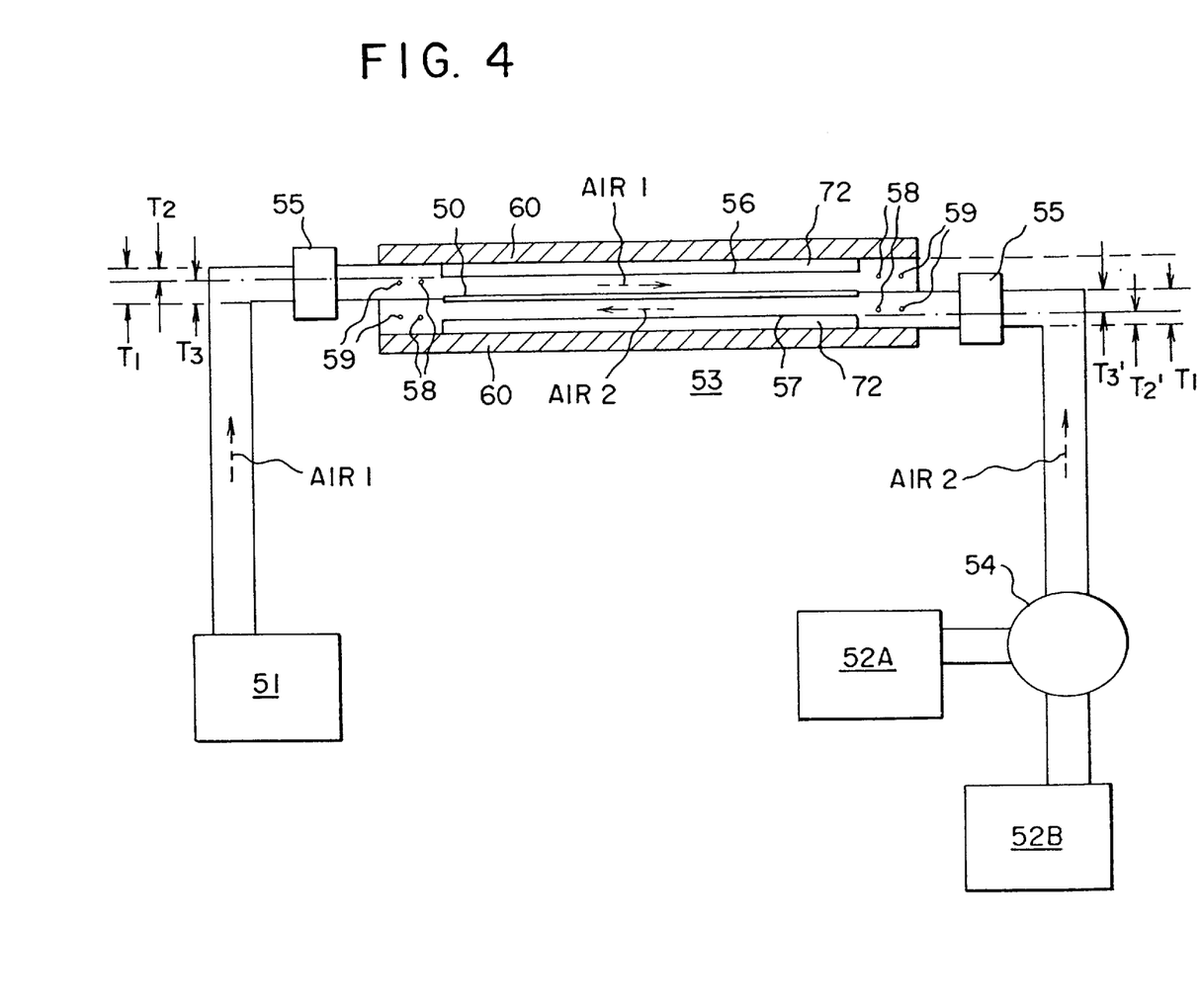
FIG. 4 is a sectional general view (taken from above) of a heat and moisture transfer characteristic measurement system of one embodiment of the present invention.
Figure 5:
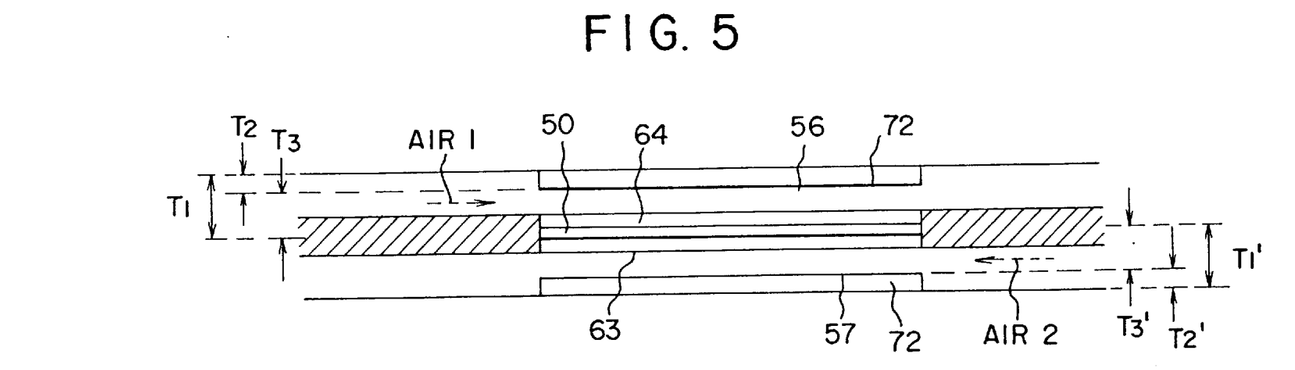
FIG. 5 is an enlarged sectional view of an essential portion of the system of FIG. 4.

FIG. 4 is a sectional general view (taken from above) of the heat and moisture transfer characteristic measurement system of one embodiment of the present invention and FIG. 5 is an enlarged sectional view of an essential portion of the system of FIG. 4. The system mainly comprises some conditioned air supply devices 51, 52A, 52B for controlling the temperature and humidity of the air to be supplied to a sample 50 to be measured and a temperature and humidity measurement section 53 for measuring the temperature and humidity of the sample 50 mounted thereon.

The conditioned air supply device 51 is used to supply the first type of air 1(hereinafter, referred to as the air 1) which has been adjusted to have predetermined temperature and humidity values while the conditioned air supply devices 52A and 52B are used to supply the second type of air 2(hereinafter, referred as the air 2) which has been adjusted to have predetermined different temperature and humidity values. The two devices 52A and 52B are connected to each other by a switching device 54 whereby the temperature and humidity of the air 2 can be switched from one to the other in a moment to thereby meet the condition of the sample 50 being tested. Further, each of the devices 51, 52A and 52B has, for example, the following performance: Temperature control range: 5~50° C.; Humidity control range: 10~90% RH; and Quantity of generation: more than 25 liters per min per line. Further, there are provided flow rate adjusters 55 midway in the pipes extending from the conditioned air supply devices 51 and 52A, 52B, respectively to the temperature and humidity variation measurement section 53. It is of course possible to provide two units of the conditioned air supply device for each of the first and second air 1 and 2 or to provide only one unit of such a device for the air or three or more units of such a device for of the air.

Figure 6:
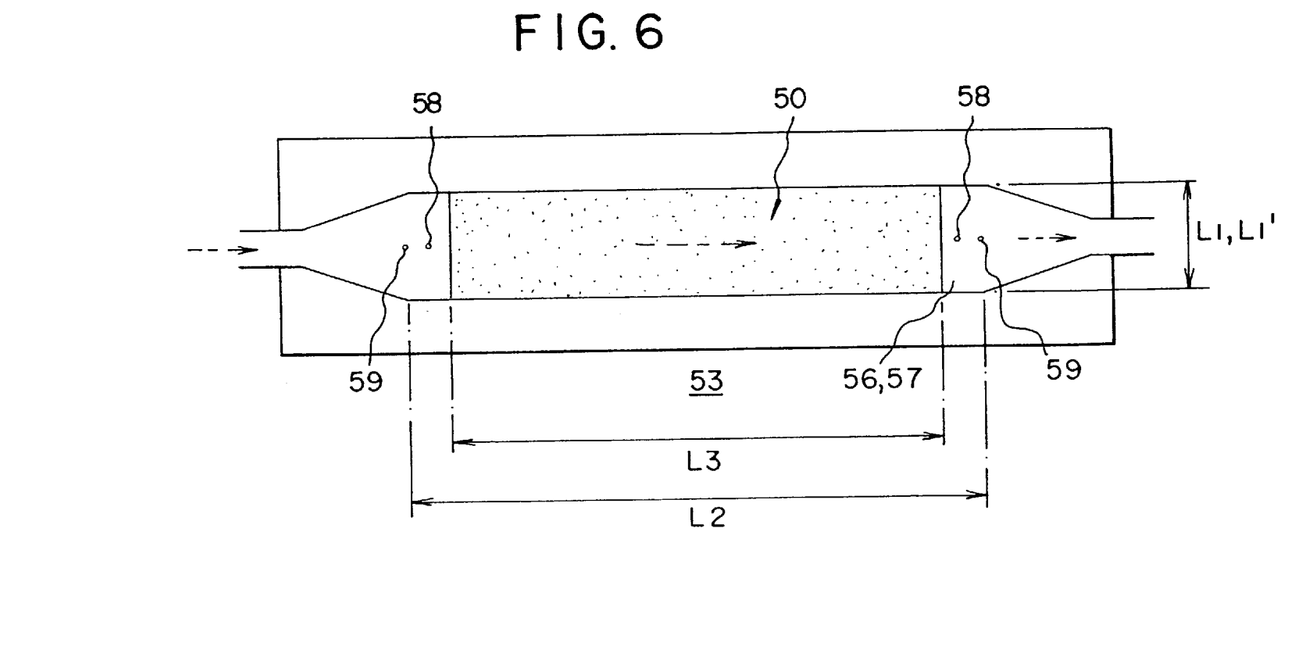
FIG. 6 is a plan view of the system of FIG. 4 when taken from the side.

Within the temperature and humidity variation measurement section 53 there are formed a pair of laminar spaces 56 and 57 as shown in FIG. 6, which shows a side view of the aforementioned section 53. In FIG. 6 reference symbols L1 and L2 designate the vertical and the horizontal dimensions of the laminar spaces 56 and 57 and the symbols L1' and L3 designate the vertical and the horizontal dimensions of the sample 50. In the shown mode, the expressions L1=L1' and L2>L3 are established so as to secure spaces for mounting sensors (to be described later) outside both ends of the laminar spaces 56 and 57. The laminar spaces 56 and 57 and the sample 50 are preferably rectangular in plane shape but other suitable shapes may be employed.

Further, within the temperature and humidity variation measurement section 53 there may be provided laminar space thickness adjustment plates 72 so as to adjust the thickness of each of the laminar spaces. In FIG. 5, reference symbols T1 and T1' respectively designate the thicknesses of the laminar spaces 56 and 57 in the absence of the adjustment plates 72, reference symbols T2 and T2' respectively designate the thicknesses of the adjustment plates 72 and reference symbols T3 and T3' respectively designate the thicknesses of the laminar spaces which are in contact with the sample 50. Accordingly, by varying the thicknesses T2 and T2' of the adjustment plates 72 while keeping constant the thicknesses T1 and T1' of the laminar spaces in the absence of the adjustment plates 72, it is possible to adjust the thicknesses T3 and T3' of the laminar spaces coming into contact with the sample 50. For example, it is possible to make L1=50 mm, L2=420 mm, L1=50 mm, L3=300 mm, T1=T1'=10 mm, T2=T2'=4 mm and T3=T3'=6 mm. The surface area of the sample 50 is desired to be 10 cm$^2$ or more because where it is less than 10 cm$^2$, the sample 50 is too small for the quantity of air to perform a satisfactory measurement. Further, it is preferable that each of T3 and T3' be in the range of between 2 mm and 15 mm and more preferably be less than 10 mm. If less than 2 mm, no measurement will be possible and if exceeding 15 mm, the thickness of each laminar space coming into contact with the sample 50 becomes too large. Further, although T1 and T1', T2 and T2', and T3 and T3' are equal to each other, respectively, in the drawings, they may be differentiated within a range which does not impair the object of the present invention. Also, if the sample 50 as a target to be measured is a cloth, it is possible to cause air, in an amount with which no adverse effect is practically produced by any disturbance due to measurement, to pass through such a thin space. Further, each of the laminar spaces 56 and 57 tapers in such a way that the inlet and outlet ports of the first and second airs 1 and 2 to be supplied from the conditioned air supply devices 51, 52A and 52B are arranged in a straight line with the inlet port expanding outward by an angle of ±10~45 degrees with respect to the center line of the inlet port and the outlet port becoming narrower by an angle of ±10~45 degrees. In this case, the most desirable angle for the entry and discharge of the air, that is, the tapering angle at which air can flow without turbulence or retention, is in the order of ±30 degrees but the present invention is of course not limited to such a numeric value.

Each of the laminar spaces 56 and 57 is in the shape of a rectangle with the area of the central portion thereof being, for example, 300×50 mm and both of the laminar spaces are separated from each other by the sample 50. When measurement is performed, the air 1 is supplied into one of the laminar spaces while the air 2 is supplied into the other. Both the airs 1 and 2 can be supplied in the same direction or in opposite directions by changing the manner of the connection of the pipes from the conditioned air supply devices 51, 52A and 52B to the temperature and humidity variation measuring section 53. Of course, it is possible to measure a plurality of samples simultaneously if the number of pairs of laminar spaces is increased and pipes extending from the conditioned air supply devices 51, 52A and 52B are provided for each pair of laminar spaces, for example.

On the sides of the air inlet and outlet ports of the laminar spaces 56 and 57 there are provided temperature sensors 58 and humidity sensors 59, respectively (note that these are integrally formed in FIG. 4). It is desirable that the performance of each temperature sensor 58 is: Response speed=less than 5 seconds; Measurement range=1~100° C.; and Measurement range accuracy=±0.01° C. and the performance of each humidity sensor 59 is: Response speed=less than 5 seconds; Measurement range=0~100% RH; and Measurement range accuracy=less than less than ±2%.

Figure 7:
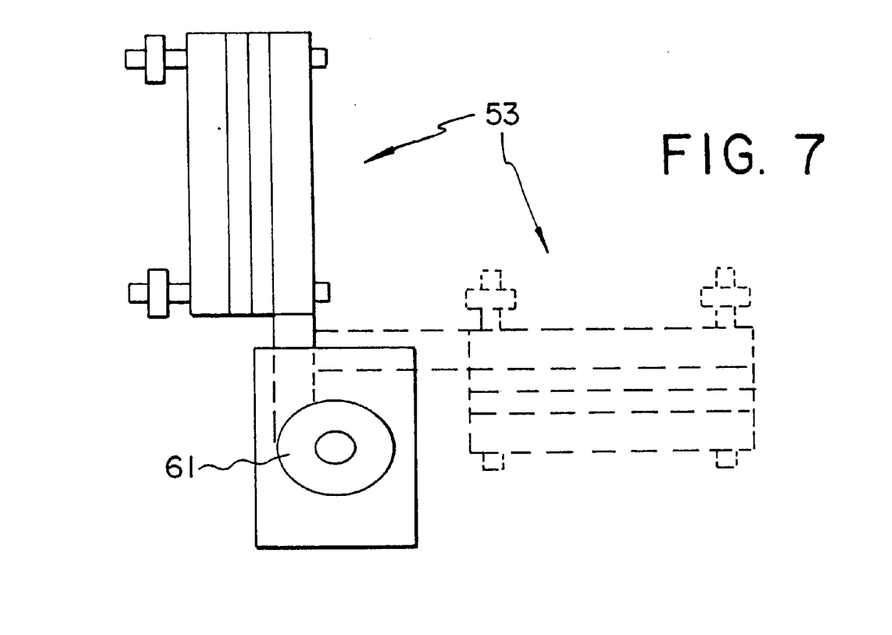
FIG. 7 is an illustration of a structure for adjusting the angle of the temperature and humidity variation measurement section of the system of FIG. 4.

The temperature and humidity variation measurement section 53 is formed within a frame or box but in order to reduce as much as possible the amount of heat exchange between a frame or wall (not shown) and the external environment, a heat insulating member 60 such as Styrofoam is provided. It is of course possible to use a material such as polycarbonate having an excellent heat insulation property for forming the laminar spaces 56 and 57. Further, it is possible to set the temperature and humidity variation measurement section 53 at a desired position within a range of 90 degrees from the vertical to the horizontal plane with respect to the setting surface or floor surface by rotating the section 53 with a space angle adjustment handle 61, as shown in FIG. 7.

Further, although not shown in the drawings, a structure may be formed in which an opening and closing type hole for dripping water-drops is formed in the outer frame of the temperature and humidity variation measurement section 53 so that a desired amount of water-drops is dripped or sprayed through the hole by using an injector. Thus, by so doing, it is possible to evaluate side by side the behavior of a cloth with respect to liquid-phase moisture and accordingly, it is possible to obtain data capable of meeting a case in which body sweat is directly adhered to a wearer's clothing at the time of body perspiration.

Figure 8:
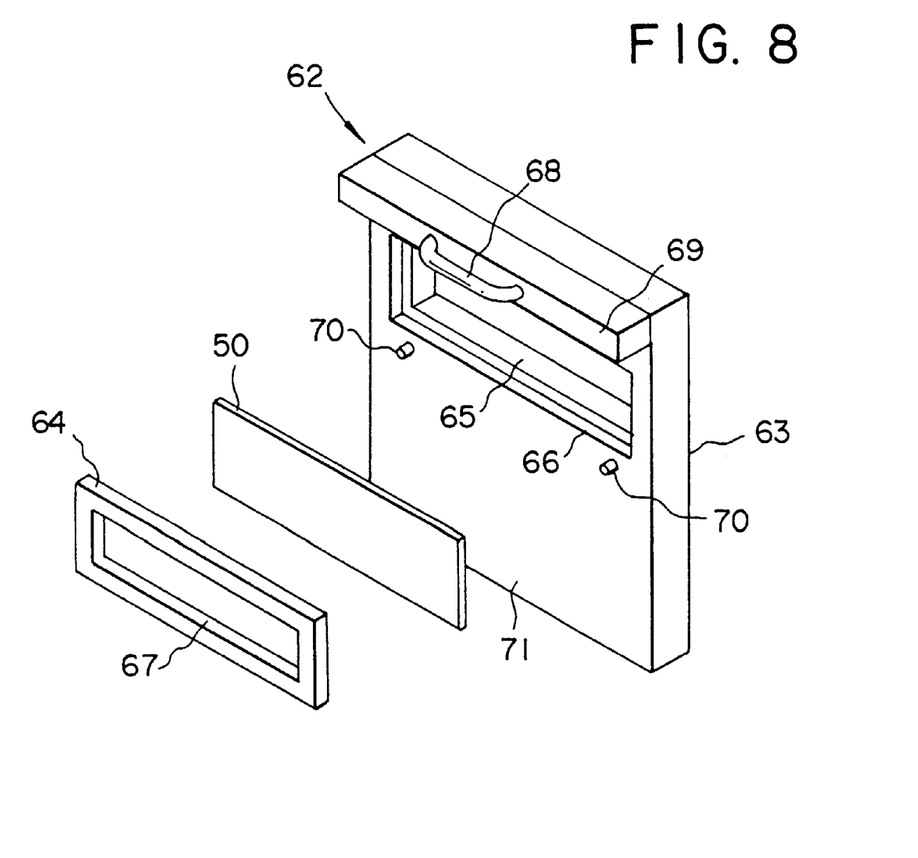
FIG. 8 is a perspective view of a sample holder used in the system of FIG. 4.

The partitioning of the laminar spaces 56 and 57 and the mounting of the sample between the two laminar spaces can be performed in such a manner that a dedicated sample holder 62, as shown in FIG. 8 is used to mount the sample 50 between the two laminar spaces 56 and 57 in a moment. The sample holder 62 mainly comprises a holder body 63 and a sample stop frame 64. The holder body 63 has an opening 65 and a concave portion 66 formed around the former and the sample stop frame 64 also has an opening 67 which is the same in shape as the opening 65 and which has the same area as that of the sample 50. Further, it is preferable that the thickness of the holder body 63 be about 3 mm and the thickness of the sample stop frame 64 be in the range of about 1~2 mm. These dimensions are properly adjusted according to the condition of the sample 50. When the sample 50 is set in the holder body 63, the sample 50 may be put into the concave portion 66 and then the sample may be clamped by the sample stop frame 64 from above. In addition, the holder body 63 is provided with a handle 68 for mounting it on, or taking it out from, the temperature and humidity variation measurement section 53 and a projection 69 to which the handle 68 is attached, and set screws 70 for fixing the holder body 63 to the temperature and humidity variation measurement section 53. Further, the lower side portion 71 of the holder 63 below the opening 65 shown in FIG. 8 forms itself into a heat insulating section for partitioning the laminar spaces 56 and 57 when the holder 63 is attached to the temperature and humidity variation measurement section 53.

Figure 9A:
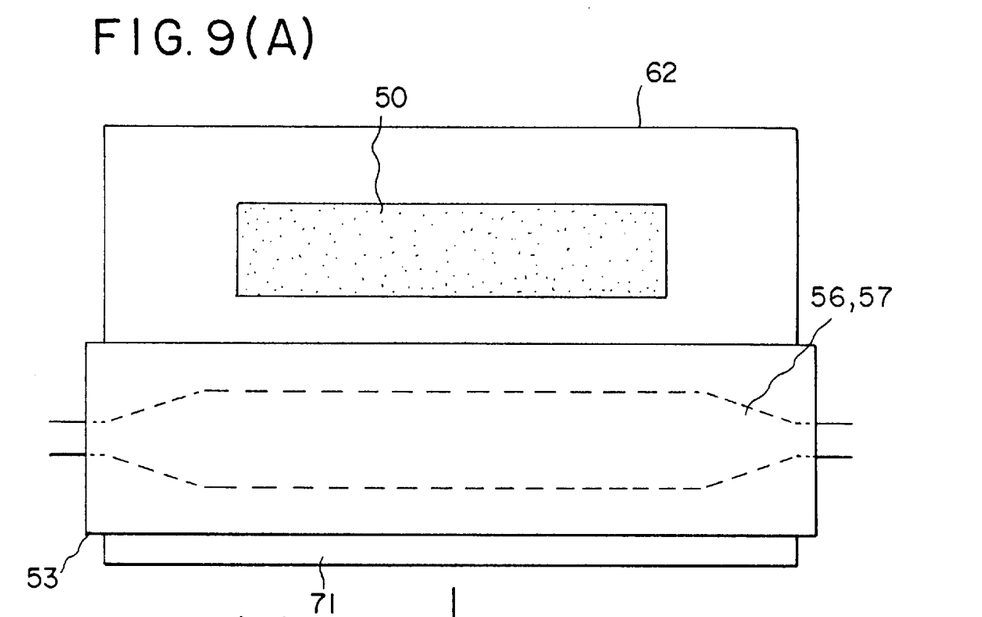
FIG. 9 is an illustration of the sample holder of FIG. 8 especially when the sample holder is in use.
Figure 9B:
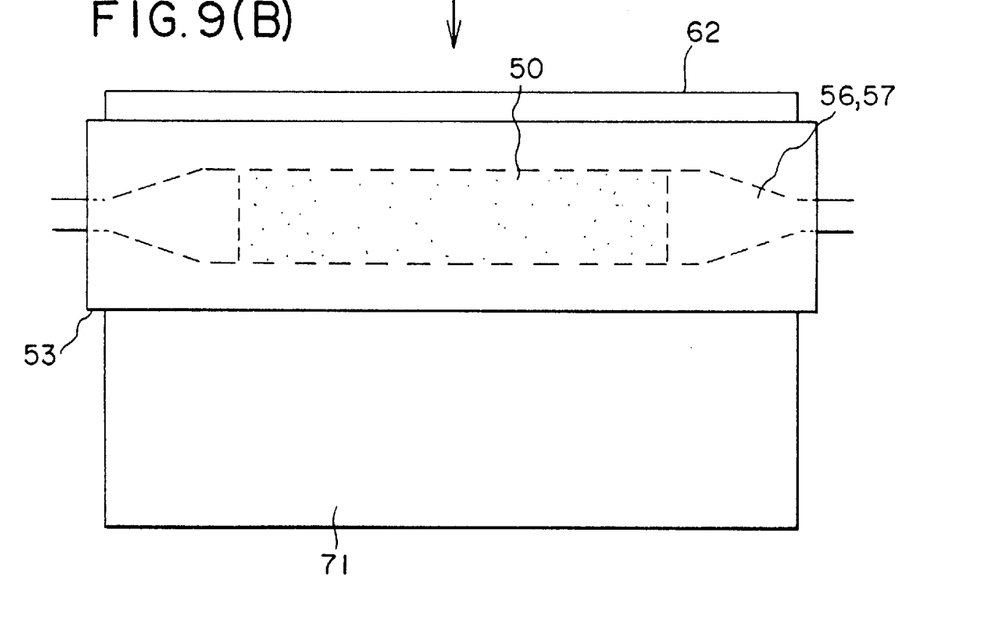
Figure 10A:
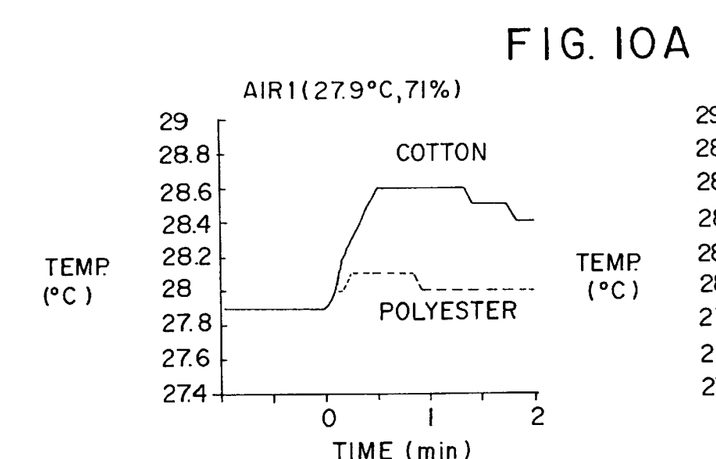
FIG. 10 is a graph showing the results of the measurement of the heat and moisture transfer characteristics of a shirting material by use of the system according to one embodiment of the invention.
Figure 10B:
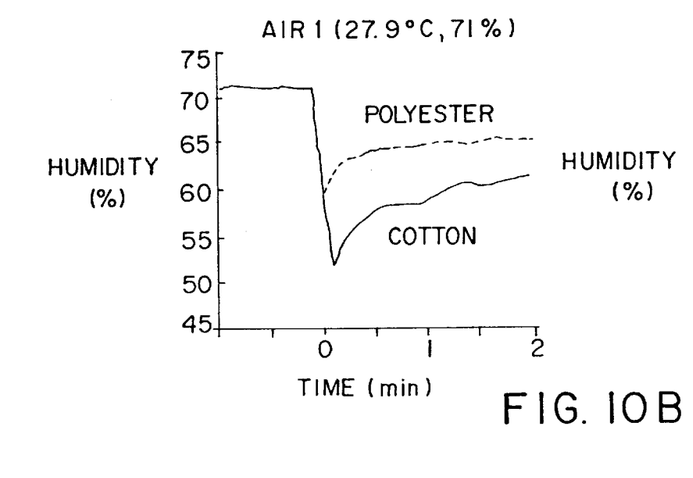
Figure 10C:
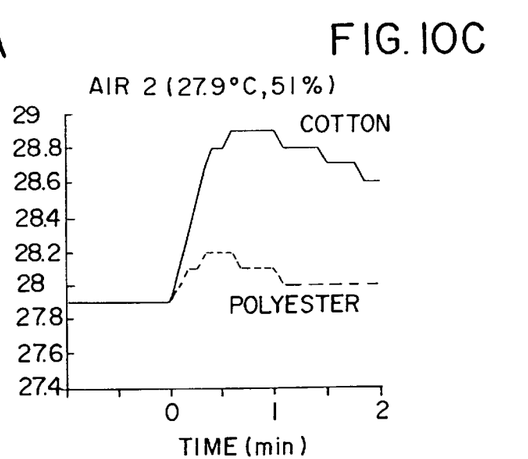
Figure 10D:
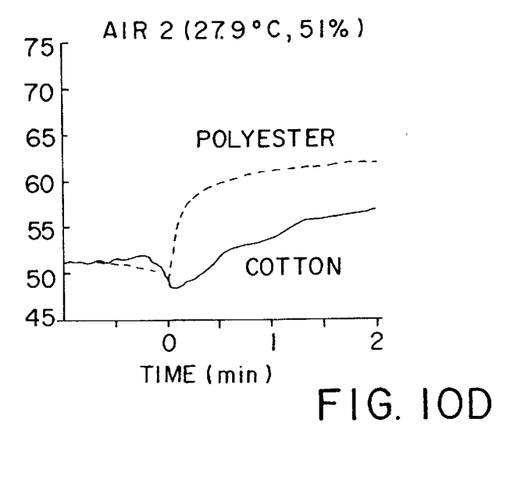

In order to attach the sample holder 62 to the temperature and humidity variation measurement section 53 at the time of testing a target material to be measured, the sample holder 62 is first set so as to allow the heat insulating portion 71 of the sample holder 62 to partition the laminar spaces 56 and 57 as shown in FIG. 9 (A). When the sample holder 62 is attached to the temperature and humidity variation measurement section 53 in a state other than horizontal, the sample holder 62 is fixed to the section 53 by means of the set screws 70, and the set screws 70 are required lest the sample holder 62 should enter between the laminar spaces 56 and 57 to such a depth as to allow the opening 65, having the sample 50 fitted therein, to come to lie therebetween. In this state, the airs 1 and 2 are allowed to flow into the laminar spaces 56 and 57, respectively, over a certain period of time and the stabilization of the temperature and humidity of each of the supplied airs in the temperature and humidity measurement section 53 is confirmed. Next, the set screws 70 are removed and as shown in FIG. 9 (B), the sample holder 62 is slid to be set in a state in which the laminar spaces 56 and 57 are partitioned by the sample 50. In this case, by the projection 69 attached with the handle 68 of the sample holder 62, the position of the sample holder 6, is fixed.

Next, the measuring operation by use of the system according to the embodiment of the present invention will be described. In the above-described state in which the sample 50 is set, the airs 1 and 2 which have been adjusted to the desired temperature and humidity flow into the temperature and humidity variation measurement section 53 in the desired amounts, respectively. The airs 1 and 2 thus supplied are brought into contact with the temperature sensor 58 and the humidity sensor 59 at the inlet port of the section 53, then, after passing through the laminar spaces 56 or 57 partitioned by the sample 50, they are brought into contact again with the temperature sensor 58 and the humidity sensor 59 on the outlet port of the section 53 and then discharged to the outside. In this case, an exchange of heat and moisture takes place between the air 1 and the air 2 through the sample 50. Accordingly, by measuring the temperature and humidity of the airs 1 and 2 at the inlet and outlet ports of the temperature and humidity variation measurement section 53, it is possible to understand the heat and moisture transfer characteristics of the sample 50. Thus, by varying the airs 1 and 2 to correspond to various temperature and humidity conditions at the outside and inside of a wearer's clothing, it is possible to measure the variations of the temperature and humidity of the air taking place through the sample 50 simultaneously and in a time-based manner.

Further, by switching the two conditioned air supply devices 52A and 52B for the laminar space 57 to vary the temperature and humidity of the air flowing through the laminar space in a moment, it is possible to produce the status of the minute space between clothing and the human body where an instantaneous change takes place due to perspiration, the air currents, body motion, etc. Data measured by the temperature and humidity sensors 58 and 59 may be supplied to a data recorder (not shown) for recording and the recorded data may be evaluated by a predetermined process. If the heat and moisture transfer characteristics of a clothing material as a target sample are measured accurately, it is possible to effectively develop a cloth capable of assuring comfortableness for wearing.

Measurement Example

A result of the measurement of the heat and moisture transfer characteristics of a shirting material obtained by the use of the system according to the above-described embodiment is shown in FIG. 10. In this measurement, the temperature and humidity of the air 1 were adjusted to 29.4° C. and 82%, respectively, by using the conditioned air supply device 51 of the system while those of the air 2 were adjusted to 29.0° C. and 50%, respectively, by using the conditioned air supply device 52A in an external environment having a temperature of 27° C. and a humidity of 60%. The sample had been placed in an atmosphere having the external environment temperature of 27° C. and a humidity of 60% before the sample was put into the system. Further, the flow rate of each of the airs 1 and 2 was set to 10 liters per min and after making sure that the temperature and humidity of each of the airs 1 and 2 were stabilized in the temperature and humidity variation measurement section 53, the sample was instantaneously mounted between the laminar spaces 56 and 57 by using the dedicated sample holder 62. As sample materials, a shirting material consisting of 100% cotton and a shirting material consisting of 100% polyester both of which materials have different moisture absorbent properties were used.

As a result of the above-described measurements, time based variations in the temperature and humidity of each of the airs 1 and 2 shown in FIG. 10 were obtained. As will be clear from the figure, it can be clearly read from the interrelationship between the temperature and humidity that there is an outstanding difference between cotton and polyester with respect to their heat and moisture transfer characteristics. Incidentally, there can be observed from FIG. 10 a rise in the temperature of the cotton shirting material and this is considered due to the influence of the absorption heat resulting from the absorption of moisture by the cotton.

Further, by changing the temperature and humidity conditions of the airs 1 and 2, adjusting the flow rate of each of the airs 1 and 2 and switching from the air 2 to the other type of air 3, various conditions of wearing such clothing can be reproduced and the heat and moisture transfer characteristics of clothing materials corresponding to such conditions can be measured definitely as described above.

Advantages of the Invention

The heat and moisture transfer characteristic measurement system according to the first embodiment of the present application has various advantages, namely: the variations of the temperature and humidity of the air through a sample by forming various temperature and humidity conditions of the outside and inside of the clothing can be measured simultaneously and in a time-change base manner and the variations of the heat and moisture taking place within the minute space between clothing and the human body due to perspiration can be accurately measured and evaluated.

The heat and moisture transfer characteristic measurement system according to the second embodiment of the present application has various advantages, namely: due to the provision of the two conditioned air supply units for air to be supplied into one of the laminar spaces for the purpose of supplying airs having different temperature and humidity values instantaneously by the changeover device, it is possible to set a condition in which the instantaneous change that takes place in the minute space between clothing and the human body due to perspiration can be duplicated so that the behavior of the target sample in varying condition, can be measured.

The heat and moisture transfer characteristic measurement system according to the third embodiment of the present application has an advantage as well as the aforementioned common advantages, namely: since the heat and moisture transfer characteristic measurement system includes means for changing the condition of the system with respect to its setting surface, data regarding the various setting modes of the system can be obtained with ease.

The heat and moisture transfer characteristic measurement system according to the fourth embodiment of the present application has an advantage as well as the aforementioned common advantages, namely: since the system includes means for dripping water-drops onto the target sample, the behavior of the sample with respect to a certain quantity of liquid-phase moisture such as perspiration can be measured and evaluated.

The heat and moisture transfer characteristic measurement system according to the fifth embodiment of the present application has an advantage as well as the aforementioned common advantages, namely: due to the provision of the temperature and humidity variation detection means at the inlet and outlet ports of the laminar spaces so as to detect the variations of the temperature and humidity of the air taking place as a result of the heat and moisture transfer characteristics between the air passing through each of the laminar spaces and the sample, it is possible to measure and evaluate the temperature and humidity variations of the air in the minute space like that between clothing and the human body.

The heat and moisture transfer characteristic measurement system according to the sixth embodiment of the present application has an advantage as well as the aforementioned common advantages, namely: due to the arrangement in which the air passage means can be attached from the side of any of the pair of laminar spaces, data on various flow modes of air can be sampled.

The heat and moisture transfer characteristic measurement system according to the seventh embodiment of the present application has an advantage as well as the aforementioned common advantages, namely: since the thickness of each of the laminar spaces is set to a value of less than 15 mm, data can be sampled by reproducing a thin space like that between clothing and the human body.

The heat and moisture transfer characteristic measurement system according to the eight embodiment of the present application has an advantage as well as the aforementioned common advantages, namely: since the system makes use of a sample mounting jig having an opening for exposing the target sample to any of the pair of laminar spaces, the mounting and removal of the sample can be made instantaneously and with ease.

The heat and moisture transfer characteristic measurement system according to the ninth embodiment of the present application has an advantage as well as the aforementioned common advantages, namely: since the area of the opening of the sample mounting jig is 10 cm$^2$ or more, the sample can never be too small for the quantity of air thereby allowing satisfactory measurement to be performed.

The heat and moisture transfer characteristic measurement system according to the tenth embodiment of the present application has an advantage as well as the aforementioned common advantages, namely: since the system has two or more laminar spaces, more than two target samples can be measured simultaneously.

What is claimed is:

1. A heat and moisture transfer characteristic measurement system for thin materials comprising means for forming a laminar air flow space on each side of a target sample material to be measured; a pair of air passage means for providing two types of air, each adjusted to have predetermined temperature and humidity values, one of said two types of air to pass through one of said laminar spaces and the other of said two types of air to pass through the other of said laminar spaces; and means for detecting temperature and humidity variations in each of said laminar spaces, one of said pair of air passage means being provided with two conditioned air supply units and a changeover device for switching between air supply units so as to instantaneously supply air having different temperature and humidity values; wherein a removable sample holder is provided between said pair of laminar spaces, said holder having an opening capable of causing the target sample mounted thereon to be exposed to any said laminar spaces.

2. A heat and moisture transfer characteristic measurement system according to claim 1 which is provided with means for varying an angle of said space forming means with respect to a horizontal surface.

3. A heat and moisture transfer characteristic measurement system according to claim 1 wherein a means for detecting temperature and a means for detecting humidity are provided at each of an inlet and an outlet of each of said laminar spaces whereby the temperature and moisture variations of air generated as a result of transfer of heat and moisture between the airs passing through said laminar spaces and said target sample are detected.

4. A heat and moisture transfer characteristic measurement system according to claim 1, wherein each of said pair of air passage means can be attached to said laminar space forming means from either end of said laminar spaces.

5. A heat and moisture transfer characteristic measurement system according to claim 1, wherein the thickness of each of said pair of laminar spaces is less than 15 mm.

6. A heat and moisture transfer characteristic measurement system according to claim 1, wherein the area of the opening of said sample mounting holder is in the order of at least 10 cm$^2$.

7. A heat and moisture transfer characteristic measurement system according to claim 1, wherein at least two pairs of said laminar spaces are provided.

* * * * *